United States Patent
Yeh

(10) Patent No.: US 11,102,870 B1
(45) Date of Patent: Aug. 24, 2021

(54) LIGHTING DEVICE WITH PHYSIOLOGICAL DIMMING AND DIMMING METHOD FOR THE SAME

(71) Applicant: LRU TECHNOLOGY INC., Taipei (TW)

(72) Inventor: Lu-Sung Yeh, New Taipei (TW)

(73) Assignee: LRU TECHNOLOGY INC., Taipei (TW)

( * ) Notice: Subject to any disclaimer, the term of this patent is extended or adjusted under 35 U.S.C. 154(b) by 0 days.

(21) Appl. No.: 17/035,957

(22) Filed: Sep. 29, 2020

(30) Foreign Application Priority Data

Aug. 12, 2020 (TW) ................................. 109127304

(51) Int. Cl.
*H05B 45/10* (2020.01)
*H05B 47/11* (2020.01)
*H05B 47/16* (2020.01)
*A61N 5/06* (2006.01)
*H05B 47/115* (2020.01)
*H05B 45/20* (2020.01)

(52) U.S. Cl.
CPC ........... *H05B 47/11* (2020.01); *A61N 5/0618* (2013.01); *H05B 45/20* (2020.01); *H05B 47/115* (2020.01); *H05B 47/16* (2020.01)

(58) Field of Classification Search
CPC ........ H05B 45/00; H05B 45/10; H05B 45/20; H05B 47/10; H05B 47/11; H05B 47/115; H05B 47/16; A61N 5/0618
See application file for complete search history.

(56) References Cited

U.S. PATENT DOCUMENTS

| | | | | |
|---|---|---|---|---|
| 2013/0229113 A1* | 9/2013 | Toda | ............... | H05B 47/105 |
| | | | | 315/152 |
| 2017/0238392 A1* | 8/2017 | Shearer | ............. | H05B 45/10 |
| | | | | 315/153 |

FOREIGN PATENT DOCUMENTS

| CN | 110168445 A | 8/2019 |
|---|---|---|
| CN | 111050444 A | 4/2020 |
| TW | 202015491 A | 4/2020 |
| TW | 202019235 A | 5/2020 |

* cited by examiner

*Primary Examiner* — Jimmy T Vu
(74) *Attorney, Agent, or Firm* — Li & Cai Intellectual Property (USA) Office

(57) ABSTRACT

A lighting device with physiological dimming and a dimming method for the same are provided. The lighting device includes a lighting unit with lighting modules, a light sensor, and a control circuit. According to a first illumination requirement and a light sensing value of the light sensor, the control circuit controls the lighting unit to output a first illumination light source that meets a first predetermined illuminance in a first time slot. According to a second illumination requirement and the light sensing value, the control circuit controls the lighting unit to output a second illumination light source that meets a second predetermined illuminance in a second time slot. According to the first and the second illumination requirements, the control circuit dynamically controls lighting from any one or a combination of the lighting modules, such that the lighting unit generates correspondingly the first and the second illumination light sources.

20 Claims, 5 Drawing Sheets

LIGHTING DEVICE WITH PHYSIOLOGICAL DIMMING AND DIMMING METHOD FOR THE SAME

CROSS-REFERENCE TO RELATED PATENT APPLICATION

This application claims the benefit of priority to Taiwan Patent Application No. 109127304, filed on Aug. 12, 2020. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a lighting device, and more particularly to a lighting device with physiological dimming and a dimming method for the same.

BACKGROUND OF THE DISCLOSURE

Conventional lighting devices provide more and more lighting options, rather than being limited to just a single light source. Accordingly, a lighting device that is capable of providing different illumination light sources for multi-stages can effectively satisfy people's need for various light sources in daily life. In terms of manipulating the illumination light sources for multi-stages in the lighting device, a user may select one of the illumination light sources for multi-stages as a current light source by switching a switch. While controlling of the conventional lighting devices is mostly carried out manually, a spectrum for each different illumination light source cannot be adjusted corresponding to the current physical condition of a person. Moreover, the secretion of melatonin not only changes in a human body according to different time slots of a day, but would also be affected by specific spectrums of the illumination light source.

SUMMARY OF THE DISCLOSURE

In response to the above-referenced technical inadequacies, the present disclosure provides a lighting device with physiological dimming and a dimming method, which are capable of having a corresponding illumination light source being automatically generated according to each different time slot.

In one aspect, the present disclosure provides a lighting device with physiological dimming that includes a lighting unit, a light sensor, and a control circuit. The lighting unit includes a plurality of lighting modules, and the control circuit is electrically connected to the lighting unit and the light sensor. According to a first illumination requirement and a light sensing value of the light sensor, the control circuit controls the lighting unit to output a first illumination light source that meets a first predetermined illuminance in a first time slot. According to a second illumination requirement and the light sensing value of the light sensor, the control circuit controls the lighting unit to output a second illumination light source that meets a second predetermined illuminance in a second time slot. Compared with the second illumination light source, the first illumination light source has a spectrum with higher melatonin suppression in humans. According to the first illumination requirement and the second illumination requirement, the control circuit dynamically controls lighting from any one or a combination of the plurality of lighting modules, such that the lighting unit generates the first illumination light source and the second illumination light source that correspond to the first illumination requirement and the second illumination requirement, respectively.

In another aspect, the present disclosure provides a lighting device with physiological dimming that includes a lighting unit, a light sensor, and a control circuit. The lighting unit includes a plurality of lighting modules. The control circuit is electrically connected to the lighting unit and the light sensor. According to a first illumination requirement and a light sensing value of the light sensor, the control circuit controls the lighting unit to output a first illumination light source that meets a first predetermined illuminance in a first time slot. According to a second illumination requirement, the control circuit controls the lighting unit to output a second illumination light source that meets a second predetermined illuminance in a second time slot. The first illumination light source and the second illumination light source each have a spectrum that is different from each other in terms of melatonin suppression in humans. According to the first illumination requirement and the second illumination requirement, the control circuit dynamically controls lighting from any one or a combination of the plurality of lighting modules, such that the lighting unit generates the first illumination light source and the second illumination light source that correspond to the first illumination requirement and the second illumination requirement, respectively.

In yet another aspect, the present disclosure provides a dimming method for a lighting device, which includes: detecting a light sensing value of an environment light source of the lighting device, controlling, in a first time slot, the lighting device to output a first illumination light source that meets a first predetermined illuminance according to a first illumination requirement and the light sensing value, and controlling, in a second time slot, the lighting device to output a second illumination light source that meets a second predetermined illuminance according to a second illumination requirement. The first illumination light source and the second illumination light source each have a spectrum that is different from each other in terms of melatonin suppression in humans. According to the first illumination requirement and the second illumination requirement, the lighting device dynamically controls lighting from any one or a combination of a plurality of lighting modules in the lighting device, so as to generate the first illumination light source and the second illumination light source that correspond to the first illumination requirement and the second illumination requirement, respectively. A product of multiplication of an illuminance and a circadian action factor of the first illumination light source meets the first illumination requirement, and a product of multiplication of an illuminance and a circadian action factor of the second illumination light source meets the second illumination requirement.

In summary, the lighting device with physiological dimming and the dimming method of the present disclosure are capable of providing different illumination light source outputs according to different time slots, so as to meet a current physical condition of a person. In this way, such a person can be more awake during the day and more relaxed at night. In addition, through detecting a background light source or an environment light source, a corresponding compensation is provided. Accordingly, a final output of an illumination light source would not be affected by an external light source, to thereby meet an illumination requirement.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
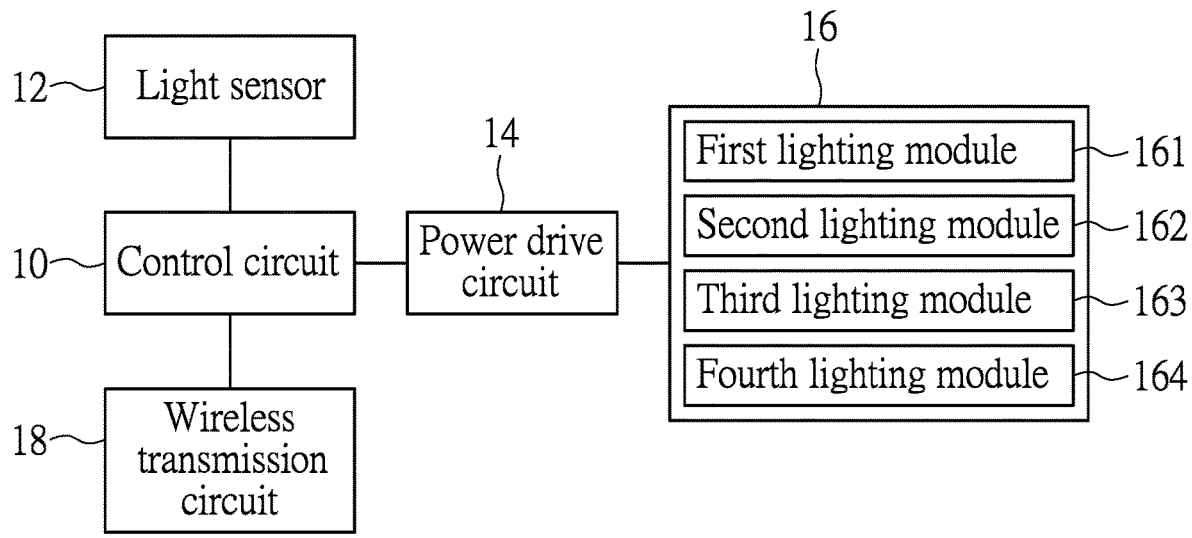
FIG. 1 is a block diagram of a lighting device with physiological dimming according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

An embodiment of the present disclosure provides a lighting device with physiological dimming and a dimming method for the same. According to a predetermined setting or an illumination requirement set by a person, the lighting device described herein is capable of depending on a time slot to provide an illumination light source that is appropriate for the person in that time slot. Further, by virtue of a spectrum of an illumination light source that varies with each time slot in terms of melatonin suppression, the person may be physically in a relatively awake or relaxed condition depending on the each time slot. In addition, to effectively overcome interference of an environment light source or a background light source with an illumination light source output by the lighting device, a compensation mechanism with which a current environment light source or background light source can be detected through light sensing is particularly provided by the lighting device of the present disclosure. With a compensation value being correspondingly generated, the illumination light source output by the lighting device undergoes a compensation adjustment. In this way, the interference caused by the environment light source or the background light source mentioned above would be sufficiently reduced. Therefore, the lighting device is capable of allowing the person to eventually feel an illumination that meets an actual illumination requirement through dynamically adjusting an output of the illumination light source.

[Embodiment of a First Hardware of a Lighting Device with Physiological Dimming]

Figure 2:
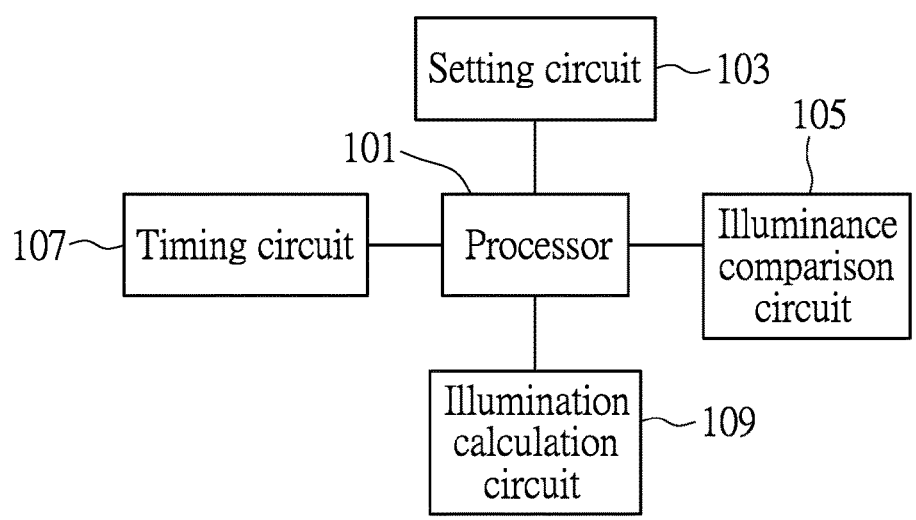
FIG. 2 is a block diagram of a control circuit according to one embodiment of the present disclosure.

Referring to FIG. 1 and FIG. 2, FIG. 1 is a block diagram of a lighting device with physiological dimming according to one embodiment of the present disclosure, and FIG. 2 is a block diagram of a control circuit according to one embodiment of the present disclosure. A lighting device 1 with physiological dimming of the present embodiment includes, for example but not limited to, a control circuit 10, a light sensor 12, a power drive circuit 14, a lighting unit 16, and a wireless transmission circuit 18. The control circuit 10 is electrically connected to the light sensor 12, the power drive circuit 14, and the wireless transmission circuit 18. The power drive circuit 14 is electrically connected to the lighting unit 16. In one embodiment, the power drive circuit 14 can also be directly integrated into the control circuit 10, such that the control circuit 10 can be in direct electrical connection with the lighting unit 16.

It is worth noting that, based on an illumination requirement, the control circuit 10 correspondingly controls the lighting unit 16 to output an illumination light source with a spectrum that varies with each different time slot in terms of melatonin suppression. For example, the illumination light source herein includes a plurality of lighting modules, and different lighting modules respectively have the same or different light-emitting characteristics. The light-emitting characteristics described herein can be, for example, any combination of color temperature, circadian action factor (CAF), and illuminance.

In addition, the illumination requirement serving as a basis of subsequent dimming for the control circuit 10 is described by taking an equivalent melanopic lux (EML) value as an example. Specifically speaking, a calculation method for the equivalent melanopic lux value is as shown in formula (1) below.

Equivalent melanopic lux (EML)=1.218*CAF*Lux

Further to the above, the control circuit 10 may achieve a standard of the illumination requirement by controlling a circadian action factor (CAF) and an illuminance (lux) of an illumination light source output by the lighting unit 16. That is to say, a product of multiplication of the circadian action factor (CAF) and the illuminance (lux) needs to meet the illumination requirement.

In one embodiment, in order for the lighting unit 16 to meet the illumination requirement, the lighting unit 16, for example, is configured to include a plurality of lighting modules, and each lighting module includes at least one light-emitting element. More specifically, the at least one light-emitting element can be, for example, an LED light-emitting element. However, the present disclosure is not limited thereto. For ease of description, the lighting unit 16 herein includes a first lighting module 161, a second lighting module 162, a third lighting module 163, and a fourth lighting module 164. The first lighting module 161 and the second lighting module 162, for example, have a same first color temperature, and each have a light source with a circadian action factor that is different from each other. The third lighting module 163 and the fourth lighting module 164, for example, have a same second color temperature, and each have a light source with a circadian action factor that is different from each other. The first color temperature can be the same as or different from the second color temperature. However, the present disclosure is not limited thereto. A combination of a color temperature and a circadian action factor for each lighting module can be arranged according to practical requirements.

Therefore, the control circuit 10 controls lighting from any one or a combination of the plurality of lighting modules in the lighting unit 16, so that an illumination light source output by the lighting unit 16 as a whole meets the illumination requirement. For example, one of the first lighting module 161, the second lighting module 162, the third lighting module 163, and the fourth lighting module 164 may emit light alone, or at least two of the aforesaid lighting modules may emit light, so that a spectrum that meets the illumination requirement in terms of melatonin suppression can be produced through a single spectrum or a mix of lights from multiple spectrums. Specifically speaking, the control circuit 10 can perform each and every lighting variation in the above-mentioned lighting unit 16 via the power drive circuit 14. The power drive circuit 14 can individually control whether or not to turn on lighting of any one of the lighting modules and control the lighting variation afterwards. Specific implementations of the power drive circuit 14 are known to those skilled in the art and will not be reiterated herein.

It is worth noting that, the control circuit 10 can obtain, through the light sensor 12, an environment light source or a background light source of where the lighting device 1 is located. Depending on a light sensing value output by the light sensor 12, the control circuit 10 determines whether or not to perform compensation with respect to an illumination light source output by the lighting device 1. For example, according to the illumination requirement, the control circuit 10 controls the lighting unit 16 to output, in different time slots, illumination light sources with spectrums that are different in terms of melatonin suppression. The illumination requirement is configured to have predetermined illuminances that correspond to different predetermined time slots.

For example, the illumination requirement is configured to have a first illumination light source with a first predetermined illuminance in a first time slot, and to have a second illumination light source with a second predetermined illuminance in a second time slot. When the control circuit 10 is in the first time slot, the control circuit 10 compares the light sensing value with the first predetermined illuminance. In a case where the light sensing value is not equal to the first predetermined illuminance, the control circuit 10 performs compensation with respect to a light source output by the lighting device 1, such that the first illumination light source meets the first predetermined illuminance. In the second time slot, the same control circuit 10 compares the light sensing value with the second predetermined illuminance. In a case where the light sensing value is not equal to the second predetermined illuminance, the control circuit 10 performs compensation with respect to a light source output by the lighting device 1, such that the second illumination light source meets the second predetermined illuminance. The above-mentioned first time slot can be, for example, a morning time period, and the second time slot can be, for example, an evening time period. Further, compared with the second illumination light source, the first illumination light source has a spectrum with higher melatonin suppression in humans. However, the present disclosure is not limited thereto. Apart from being a predetermined value, the illumination requirement can be adjusted according to personal requirements.

Furthermore, the wireless transmission circuit 18 is provided for the control circuit 18 and an external remote control device to conduct wireless transmission. For example, via the wireless transmission circuit 18, the control circuit 10 is capable of receiving a control instruction made by a person through the remote control device. The control instruction can be setting information of the illumination requirement or instructions related to controlling the turning on or off power of the lighting device 1, or adjusting color temperature or illuminance.

[Embodiment of a Control Circuit]

In one embodiment, as shown in FIG. 2, the control circuit 10 includes a processor 101, a setting circuit 103, an illuminance comparison circuit 105, a timing circuit 107, and an illumination calculation circuit 109. The processor 101 is separately in electrical connection with the setting circuit 103, the illuminance comparison circuit 105, the timing circuit 107, and the illumination calculation circuit 109.

Related information about the illumination requirement is stored in the setting circuit 103. For example, the illumination requirement received by the processor 101 through the wireless transmission circuit 18 is stored in the setting circuit 103. In one embodiment, the setting circuit 103 is a nonvolatile memory.

The illuminance comparison circuit 105 is controlled by the processor 101, and is capable of comparing a light sensing value received by the processor 101 via the light sensor 12 with the predetermined illuminance of the illumination requirement.

The timing circuit 107 is configured to provide a timing function, so that the processor 101 can control the lighting unit 16 to output illumination light sources that correspond to different time slots according to the illumination requirement.

The illumination calculation circuit 109 is used to calculate related values associated with the illumination requirement, such as the required values for an actual circadian action factor (CAF) and an actual illuminance (lux) of the illumination light source to meet the illumination requirement. The processor 101 may dynamically control lighting from any one or a combination of the lighting modules based on a calculation result of the illumination calculation circuit 109.

In one embodiment, the processor 101 firstly obtains information on the illumination requirement through the setting circuit 103. For ease of description, it is presumed that the illumination requirement has a first time slot and a second time slot, and the processor 101 controls the lighting unit 16 to output a first illumination light source that meets a first predetermined illuminance in the first time slot according to a first illumination requirement and a light sensing value. Further, the processor 101 controls the lighting unit 16 to output a second illumination light source that meets a second predetermined illuminance in the second time slot according to a second illumination requirement and the light sensing value. The processor 101 learns if the current time is in the first time slot or the second time slot through the timing function provided by the timing circuit 107.

If the current time is in the first time slot, the processor 101 obtains a light sensing value of the current location via the light sensor 12, and controls the illuminance comparison circuit 105 to compare the light sensing value with the first predetermined illuminance to obtain a compensation value. Here, the illuminance comparison circuit 105 is configured, for example, to subtract the first predetermined illuminance from the light sensing value to obtain the compensation value. If the light sensing value is greater than the first predetermined illuminance, a positive compensation value would be obtained. If the light sensing value is less than the first predetermined illuminance, a negative compensation value would be obtained. If the light sensing value is equal to the first predetermined illuminance, there would be no compensation value. The illuminance calculation circuit 109 directly performs compensation with respect to a predetermined actual illuminance according to the compensation value provided by the illuminance comparison circuit 105. Afterwards, an actual circadian action factor is calculated according to the first illumination requirement and the actual illuminance after compensation. Lastly, based on the actual illuminance and the actual circadian action factor calculated by the illuminance calculation circuit 109, the processor 101 correspondingly adjusts an illuminance of the first illumination light source output by the lighting unit 16 to meet the first predetermined illuminance. Further, a product of multiplication of an actual illuminance and a circadian action factor of the first illumination light source also meets the first illumination requirement.

Furthermore, if the current processing session is the second time slot, the processor 101 obtains a light sensing value of the current location via the light sensor 12, and controls the illuminance comparison circuit 105 to compare the light sensing value with the second predetermined illuminance to obtain a compensation value. Here, the illuminance comparison circuit 105 is configured, for example, to subtract the second predetermined illuminance from the light sensing value to obtain the compensation value. If the light sensing value is greater than the second predetermined illuminance, a positive compensation value would be obtained. If the light sensing value is less than the second predetermined illuminance, a negative compensation value would be obtained. If the light sensing value is equal to the second predetermined illuminance, there would be no compensation value. The illuminance calculation circuit 109 directly performs compensation with respect to a predetermined actual illuminance according to the compensation value provided by the illuminance comparison circuit 105. Afterwards, an actual circadian action factor is calculated according to the second illumination requirement and the actual illuminance after compensation. Lastly, based on the actual illuminance and the actual circadian action factor calculated by the illuminance calculation circuit 109, the processor 101 correspondingly adjusts an illuminance of the second illumination light source output by the lighting unit 16 to meet the second predetermined illuminance. Further, a product of multiplication of an actual illuminance and a circadian action factor of the second illumination light source also meets the second illumination requirement.

In one embodiment, the processor 101, the setting circuit 103, the illuminance comparison circuit 105, the timing circuit 107, and the illumination calculation circuit 109 can be integrated in any one or any combination of an application-specific integrated circuit (ASIC), a field programmable gate array (FPGA), a system on a chip (SoC) chip, and by cooperation of a firmware, to perform the functional operations as mentioned above.

[Flowchart Describing Dimming of the Lighting Device with Compensation for all Time Slots]

Figure 3:
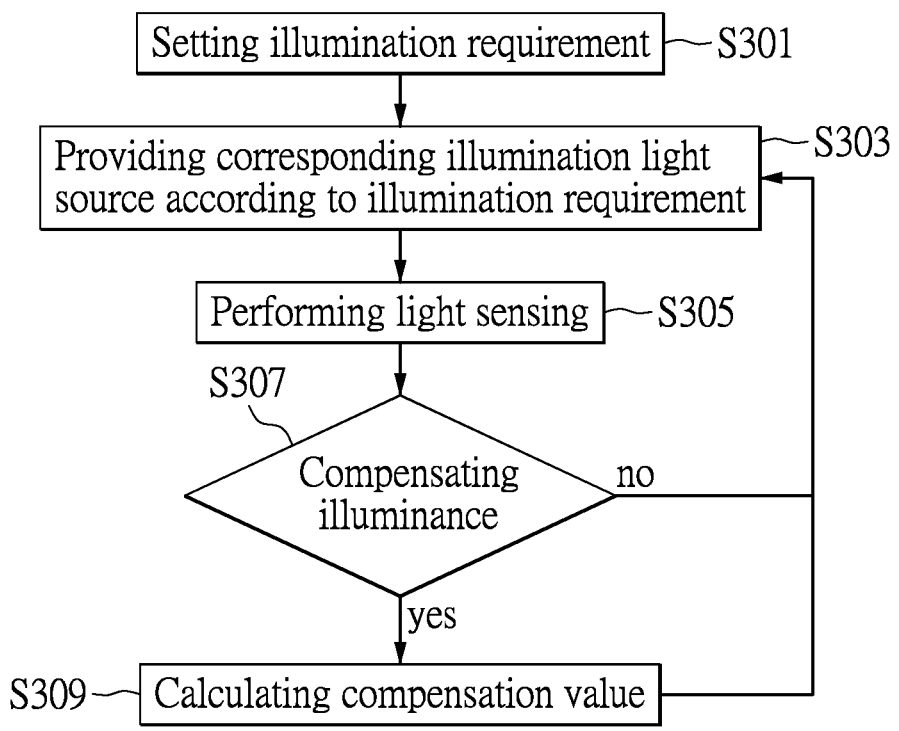
FIG. 3 is a flowchart describing a dimming of the lighting device according to one embodiment of the present disclosure.

Reference is made to FIG. 3, which is a flowchart describing a dimming of the lighting device according to one embodiment of the present disclosure. For an illustration of a lighting device as described in FIG. 3, FIG. 1 and FIG. 2 can be read in conjunction therewith. However, the flowchart as shown in FIG. 3 is not limited by the structures shown in FIG. 1 and FIG. 2.

Step S301 includes setting an illumination requirement. The control circuit 10 in the lighting device 1 obtains relevant setting information of the illumination requirement via the wireless transmission circuit 18, and with which the control circuit 10 controls lighting of the lighting unit 16.

Step S303 includes providing a corresponding illumination light source according to the illumination requirement. The control circuit 10 controls lighting from any one or a combination of the lighting modules in the lighting unit 16 in response to the illumination requirement for the current time slot.

Step S305 includes performing light sensing. The control circuit 10 controls the light sensor 12 to perform sensing with respect to a background light source or an environment light source of the lighting device 1.

Step S307 includes determining whether or not to compensate illuminance. The control circuit 10 compares a light sensing value of the light sensor 12 with a predetermined illuminance that corresponds to the current time slot. If the light sensing value is equal to the predetermined illuminance that corresponds to the current time slot, there is no need to perform illuminance compensation, and the control circuit 10 returns to step S303 for further processing. If the lighting sensing value is not equal to the predetermined illuminance that corresponds to the current time slot, it is necessary to perform illuminance compensation, and the control circuit 10 continues with step S309.

Step S309 includes calculating a compensation value. In order for an illuminance of an illumination light source output by the lighting unit 16 to meet the predetermined luminance, the control circuit 10 decreases the illuminance output by the lighting unit 16 in response to the light sensing value being greater than the predetermined illuminance, and the control circuit 10 increases the illuminance output by the lighting unit 16 in response to the light sensing value being less than the predetermined illuminance. In one embodiment, the compensation value can be obtained through a calculation method of subtracting the light sensing value from the predetermined illuminance. For example, when the predetermined illuminance is 500 lux, if the light sensing value is 600 lux, the current illuminance of the lighting unit 16 would be decreased by 100 lux. Or, when the predetermined illuminance is 500 lux, if the light sensing value is 400 lux, the current illuminance of the lighting unit 16 would be increased by 100 lux.

[Flowchart Describing Dimming of the Lighting Device with Compensation for Partial Time Slot]

Figure 4:
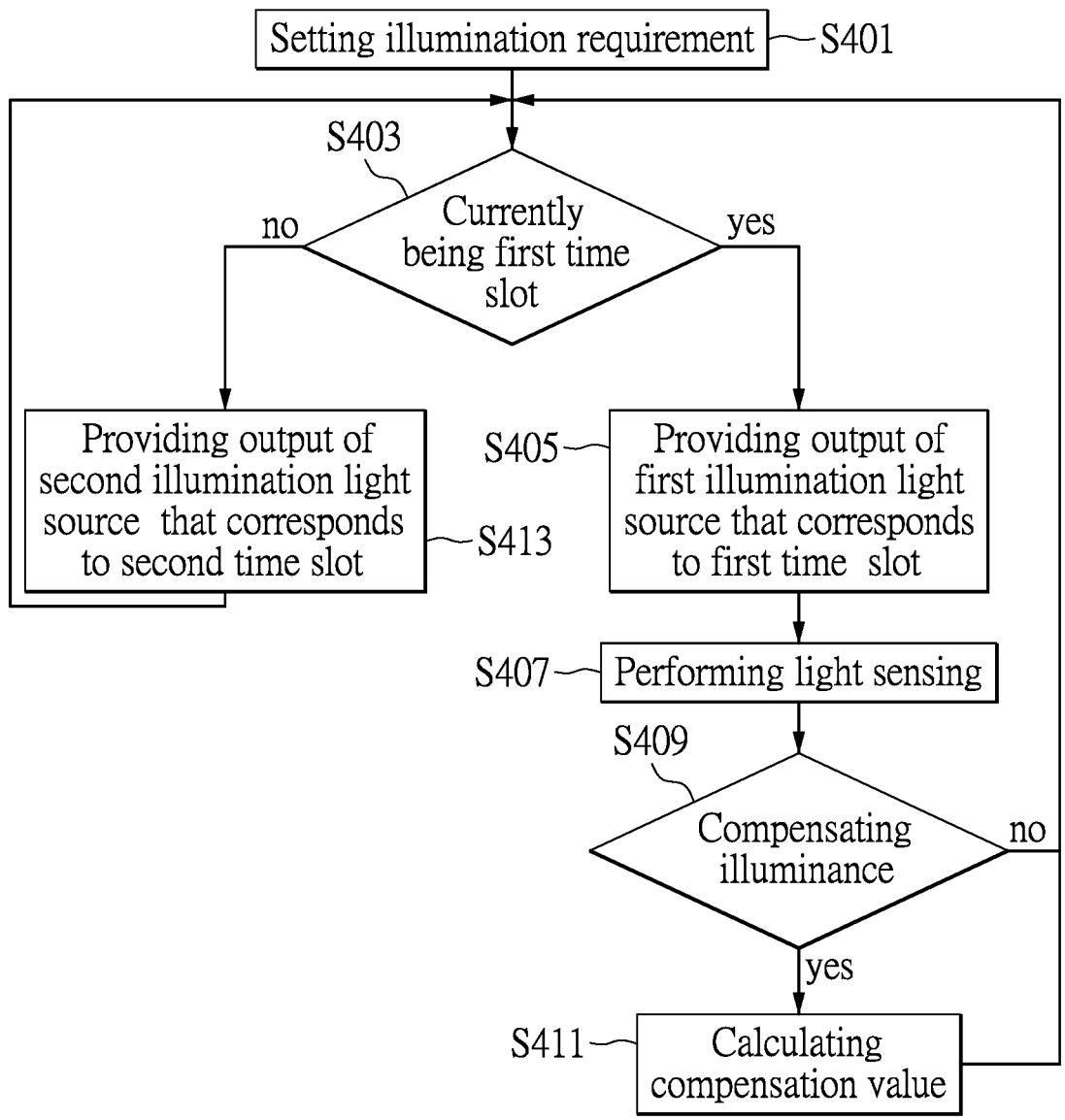
FIG. 4 is a flowchart describing the dimming of the lighting device according to one embodiment of the present disclosure.

Reference is made to FIG. 4, which is a flowchart describing the dimming of the lighting device according to one embodiment of the present disclosure. For an illustration of a lighting device as described in FIG. 4, FIG. 1 and FIG. 2 can be read in conjunction therewith. However, the flowchart as shown in FIG. 4 is not limited by the structures shown in FIG. 1 and FIG. 2.

Step S401 includes setting an illumination requirement. The control circuit 10 in the lighting device 1 obtains relevant setting information of the illumination requirement via the wireless transmission circuit 18, and with which the control circuit 10 controls lighting of the lighting unit 16.

Step S403 includes determining whether or not the current time slot is a first time slot. If it is determined to be the first time slot, step S405 is to be performed; otherwise, step S413 is to be performed.

Step S405 includes providing an output of a first illumination light source that corresponds to the first time slot. According to a first illumination requirement set in the first time slot, the control circuit 10 controls the lighting unit 16 to output the first illumination light source that meets a first predetermined illuminance.

Step S407 includes performing light sensing. The control circuit 10 controls the light sensor 12 to perform sensing with a background light source or an environment light source of the lighting device 1.

Step S409 includes determining whether or not to compensate illuminance. The control circuit 10 compares a light sensing value of the light sensor 12 with a predetermined illuminance that corresponds to the current time slot. If the light sensing value is equal to the predetermined illuminance that corresponds to the current time slot, there is no need to perform illuminance compensation, and the control circuit 10 returns to step S403 for further processing. If the lighting sensing value is not equal to the predetermined illuminance that corresponds to the current time slot, it is necessary to perform illuminance compensation, and the control circuit continues with step S411.

Step S411 includes calculating a compensation value. In order for an illuminance of an illumination light source output by the lighting unit 16 to meet the predetermined illuminance, the control circuit 10 decreases the illuminance output by the lighting unit 16 in response to the light sensing value being greater than the predetermined illuminance, and the control circuit 10 increases the illuminance output by the lighting unit 16 in response to the light sensing value being less than the predetermined illuminance.

Step S413 includes providing an output of a second illumination light source that corresponds to a second time slot. According to a second illumination requirement set in the second time slot, the control circuit 10 controls the lighting unit 16 to output the second illumination light source that meets a second predetermined illuminance.

In the flowchart as shown in FIG. 4, a light compensation mechanism is employed in the first time slot, so that an illuminance of the first illumination light source output by the lighting unit 16 would not be affected by the background light source or the environment light source. However, the light compensation mechanism is not employed in the second time slot, to thereby reduce electrical power consumption derived from the light sensor performing sensing. In one embodiment, the first time slot can be, for example, a daytime period, and the second time slot can be, for example, an evening time period. However, the present disclosure is not limited thereto.

[Embodiment of a First Hardware of a Lighting Device with Physiological Dimming]

Figure 5:
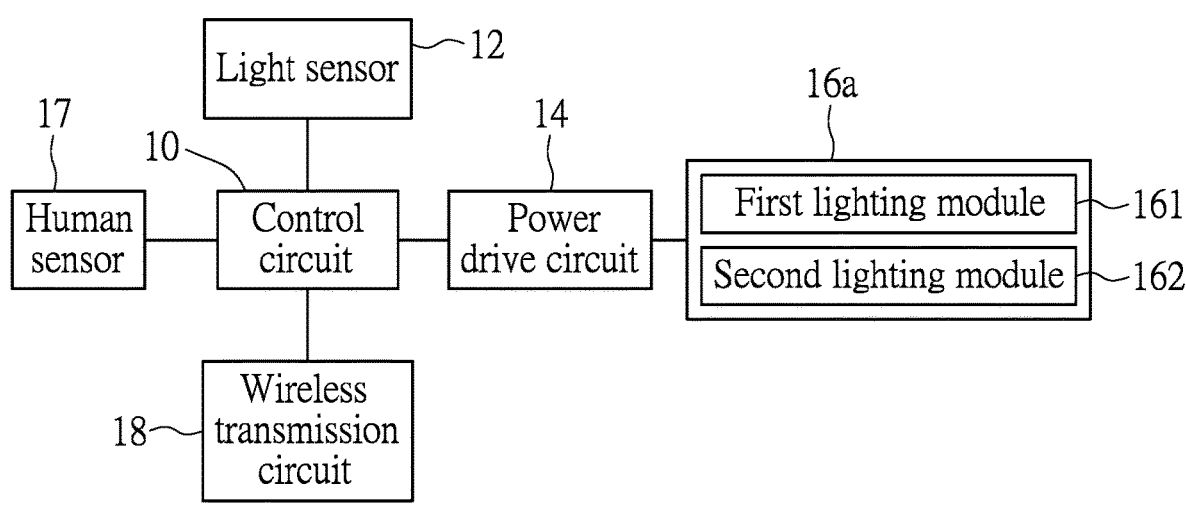
FIG. 5 is a block diagram of a lighting device with physiological dimming according to one embodiment of the present disclosure.

Reference is made to FIG. 5, which is a block diagram of a lighting device with physiological dimming according to one embodiment of the present disclosure. Compared with the lighting device 1 as shown in FIG. 1, a lighting device 2 as shown in FIG. 5 is configured to additionally include a human sensor 17. Further, a lighting unit 16a includes a first lighting module 161 and a second lighting module 162. The description of elements with the same reference numerals is the same as that recited in FIG. 1.

The human sensor 17 of the lighting device 2 as shown in FIG. 5 is electrically connected to the control circuit 10. The human sensor 17 is used to detect whether or not there is presence of a person in an area where the lighting device 2 is located. The control circuit 10 determines whether or not to turn on the light sensor 12 to perform light sensing based on a sensing result of the human sensor 17.

In one embodiment, when the human sensor 17 detects presence of a person, the control circuit 10 turns on the function of the light sensor 12, so as to employ the above-mentioned compensation mechanism and reduce unnecessary interference on an illumination requirement from an environment light source or a background light source. When the human sensor 17 detects no presence of a person, the control circuit 10 will turn off the function of the light sensor 12 or further turn off the operation of the lighting unit 16a, thereby preventing electrical power consumption.

The first lighting module 161 and the second lighting module 162 as included in the lighting unit 16a have a same color temperature, and each have a light source with a circadian action factor that is different from each other. In other embodiments, the first lighting module 161 and the second lighting module 162 each have a color temperature that is different from each other, and each have a light source with a circadian action factor that is different from each other.

[Flowchart Describing Dimming of the Lighting Device]

Figure 6:
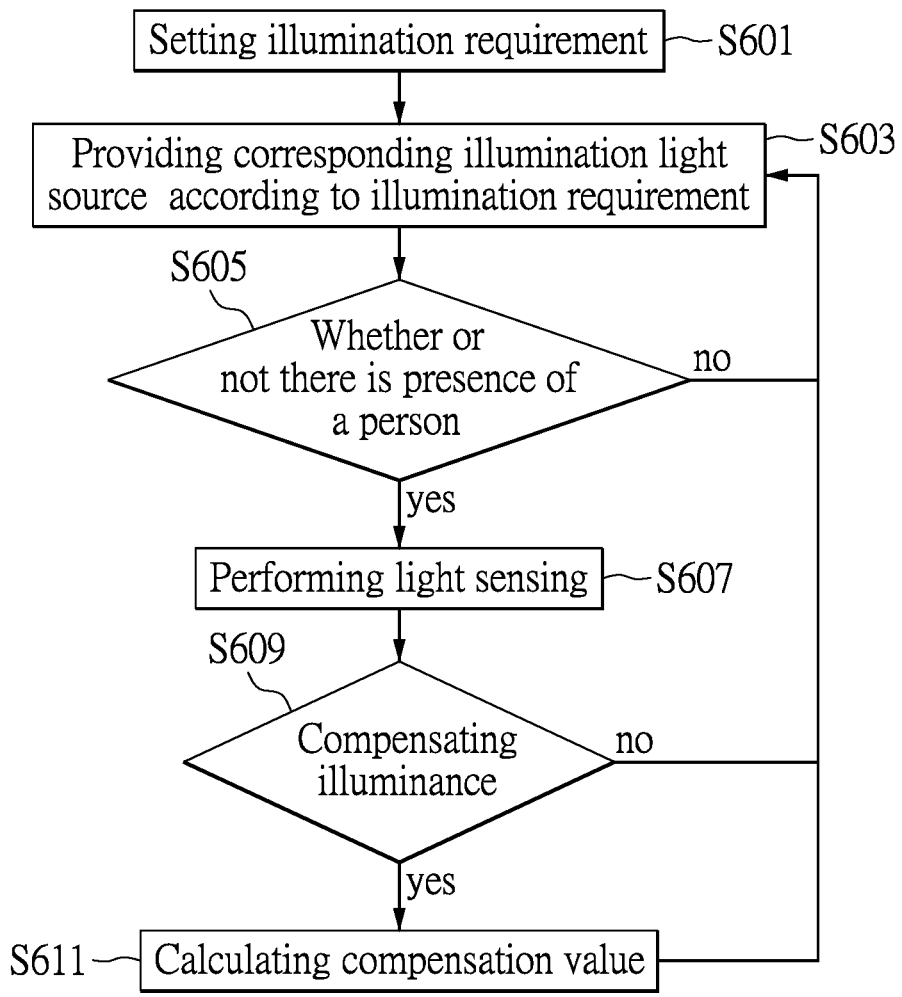
FIG. 6 is a flowchart describing the dimming of the lighting device as shown in FIG. 5 according to one embodiment of the present disclosure.

Reference is made to FIG. 6, which is a flowchart describing the dimming of the lighting device according to one embodiment of the present disclosure. For an illustration of a lighting device as described in FIG. 6, FIG. 1, FIG. 2 and FIG. 5 can be read in conjunction therewith. However, the flowchart as shown in FIG. 6 is not limited by the structures as shown in FIG. 1, FIG. 2 and FIG. 5.

Step S601 includes setting an illumination requirement. The control circuit 10 in the lighting device 2 obtains relevant setting information of the illumination requirement via the wireless transmission circuit 18, and with which the control circuit 10 controls lighting of the lighting unit 16a.

Step S603 includes providing a corresponding illumination light source according to the illumination requirement. The control circuit 10 controls lighting from any one or a combination of the lighting modules in the lighting unit 16a based on the illumination requirement for the current time slot.

Step S605 includes determining whether or not there is presence of a person. The control circuit 10 determines whether or not there is presence of a person in an area where the lighting device 2 is located. If it is determined that there is presence of a person, step S607 is to be performed; otherwise, step S603 is to be performed.

Step S607 includes performing light sensing. The control circuit 10 controls the light sensor 12 to perform sensing with a background light source or an environment light source of the lighting device 2.

Step S609 includes determining whether or not to compensate illuminance. The control circuit 10 compares a light sensing value of the light sensor 12 with a predetermined illuminance that corresponds to the current time slot. If the light sensing value is equal to the predetermined illuminance that corresponds to the current time slot, there is no need to perform illuminance compensation, and the control circuit 10 returns to step S603 for further processing. If the lighting sensing value is not equal to the predetermined illuminance that corresponds to the current time slot, it is necessary to perform illuminance compensation, and the control circuit 10 continues with step S611.

Step S611 includes calculating a compensation value. In order for an illuminance of an illumination light source output by the lighting unit 16a to meet the predetermined luminance, the control circuit 10 decreases the illuminance output by the lighting unit 16a in response to the light sensing value being greater than the predetermined illuminance, and the control circuit 10 increases the illuminance output by the lighting unit 16a in response to the light sensing value being less than the predetermined illuminance.

[Beneficial Effects of the Embodiments]

The lighting device with physiological dimming and the dimming method of the present disclosure are capable of meeting a current physical condition of a person through providing suitable illumination light sources according to different time slots. In this way, such a person can be more awake during the day and more relaxed at night. In addition, by employing the light compensation mechanism, interference from the background light source or the environment light source can be effectively reduced. Accordingly, a final output of the illumination light source may accurately meet the illumination requirement.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A lighting device with physiological dimming, comprising:
    a lighting unit including a plurality of lighting modules;
    a light sensor; and
    a control circuit being electrically connected to the lighting unit and the light sensor, wherein, according to a first illumination requirement and a light sensing value of the light sensor, the control circuit controls the lighting unit to output a first illumination light source that meets a first predetermined illuminance in a first time slot; wherein, according to a second illumination requirement and the light sensing value of the light sensor, the control circuit controls the lighting unit to output a second illumination light source that meets a second predetermined illuminance in a second time slot;
    wherein compared with the second illumination light source, the first illumination light source has a spectrum with higher melatonin suppression in humans;
    wherein, according to the first illumination requirement and the second illumination requirement, the control circuit dynamically controls lighting from any one or a combination of the plurality of lighting modules, such that the lighting unit generates the first illumination light source and the second illumination light source that correspond to the first illumination requirement and the second illumination requirement, respectively.

2. The lighting device according to claim 1, wherein the control circuit compares the light sensing value with the first predetermined illuminance in the first time slot; wherein, in order for an illuminance output of the first illumination light source to meet the first predetermined illuminance, the control circuit decreases an illuminance output by the lighting unit in response to the light sensing value being greater than the first predetermined illuminance, and the control circuit increases the illuminance output by the lighting unit in response to the light sensing value being less than the first predetermined illuminance; wherein the control circuit compares the light sensing value with the second predetermined illuminance in the second time slot; and wherein, in order for an illuminance output of the second illumination light source to meet the second predetermined illuminance, the control circuit decreases an illuminance output by the lighting unit in response to the light sensing value being greater than the second predetermined illuminance, and the control circuit increases the illuminance output by the lighting unit in response to the light sensing value being less than the second predetermined illuminance.

3. The lighting device according to claim 2, wherein, after the control circuit increases the illuminance output by the lighting unit or decreases the illuminance output by the lighting unit in the first time slot, the control circuit correspondingly adjusts lighting from a combination of the plurality of lighting modules in the lighting unit, such that a product of multiplication of an illuminance and a circadian action factor of the first illumination light source meets the first illumination requirement; and wherein, after the control circuit increases the illuminance output by the lighting unit or decreases the illuminance output by the lighting unit in the second time slot, the control circuit correspondingly adjusts lighting from a combination of the plurality of lighting modules in the lighting unit, such that a product of multiplication of an illuminance and a circadian action factor of the second illumination light source meets the second illumination requirement.

4. The lighting device according to claim 2, further comprising a human sensor, the control circuit being electrically connected to the human sensor, wherein the human sensor is used to detect whether or not there is presence of a person in an area where the lighting device is located and the control circuit determines whether or not to turn on the light sensor to perform light sensing based on a sensing result of the human sensor.

5. The lighting device according to claim 1, wherein the first illumination requirement and the second illumination requirement are each an equivalent melanopic lux (EML)

value that is different from each other, and any one of the plurality of lighting modules includes at least one light-emitting element.

6. The lighting device according to claim 1, wherein the plurality of lighting modules include a first lighting module and a second lighting module; and wherein the first lighting module and the second lighting module have a same color temperature, and each have a light source with a circadian action factor that is different from each other.

7. The lighting device according to claim 1, wherein the plurality of lighting modules include a first lighting module and a second lighting module; and wherein the first lighting module and the second lighting module each have a color temperature that is different from each other, and each have a light source with a circadian action factor that is different from each other.

8. The lighting device according to claim 1, wherein the plurality of lighting modules include a first lighting module, a second lighting module, a third lighting module, and a fourth lighting module; wherein the first lighting module and the second lighting module have a same first color temperature, and each have a light source with a circadian action factor that is different from each other; wherein the third lighting module and the fourth lighting module have a same second color temperature, and each have a light source with a circadian action factor that is different from each other; and wherein the first color temperature is different from the second color temperature.

9. A lighting device with physiological dimming, comprising:
   a lighting unit including a plurality of lighting modules;
   a light sensor; and
   a control circuit being electrically connected to the lighting unit and the light sensor, wherein, according to a first illumination requirement and a light sensing value of the light sensor, the control circuit controls the lighting unit to output a first illumination light source that meets a first predetermined illuminance in a first time slot; wherein, according to a second illumination requirement, the control circuit controls the lighting unit to output a second illumination light source that meets a second predetermined illuminance in a second time slot;
   wherein the first illumination light source and the second illumination light source each have a spectrum that is different from each other in terms of melatonin suppression in humans;
   wherein, according to the first illumination requirement and the second illumination requirement, the control circuit dynamically controls lighting from any one or a combination of the plurality of lighting modules, such that the lighting unit generates the first illumination light source and the second illumination light source that correspond to the first illumination requirement and the second illumination requirement, respectively.

10. The lighting device according to claim 9, wherein the control circuit compares the light sensing value with the first predetermined illuminance in the first time slot; and wherein, in order for an illuminance output of the first illumination light source to meet the first predetermined illuminance, the control circuit decreases an illuminance output by the lighting unit in response to the light sensing value being greater than the first predetermined illuminance, and the control circuit increases the illuminance output by the lighting unit in response to the light sensing value being less than the first predetermined illuminance.

11. The lighting device according to claim 10, wherein, after the control circuit increases the illuminance output by the lighting unit or decreases the illuminance output by the lighting unit in the first time slot, the control circuit correspondingly adjusts lighting from a combination of the plurality of lighting modules in the lighting unit, such that a product of multiplication of an illuminance and a circadian action factor of the first illumination light source meets the first illumination requirement.

12. The lighting device according to claim 10, wherein the control circuit correspondingly adjusts lighting from a combination of the plurality of lighting modules in the lighting unit in the second time slot, such that a product of multiplication of an illuminance and a circadian action factor of the second illumination light source meets the second illumination requirement.

13. The lighting device according to claim 9, wherein the first illumination requirement and the second illumination requirement are each an equivalent melanopic lux (EML) value that is different from each other, and any one of the plurality of lighting modules includes at least one light-emitting element.

14. The lighting device according to claim 9, wherein the plurality of lighting modules include a first lighting module and a second lighting module; and wherein the first lighting module and the second lighting module have a same color temperature, and each have a light source with a circadian action factor that is different from each other.

15. The lighting device according to claim 9, wherein the plurality of lighting modules include a first lighting module and a second lighting module; and wherein the first lighting module and the second lighting module each have a color temperature that is different from each other, and each have a light source with a circadian action factor that is different from each other.

16. The lighting device according to claim 9, wherein the plurality of lighting modules include a first lighting module, a second lighting module, a third lighting module, and a fourth lighting module; wherein the first lighting module and the second lighting module have a same first color temperature, and each have a light source with a circadian action factor that is different from each other; wherein the third lighting module and the fourth lighting module have a same second color temperature, and each have a light source with a circadian action factor that is different from each other; and wherein the first color temperature is different from the second color temperature.

17. A dimming method for a lighting device, comprising:
   detecting a light sensing value of an environment light source of the lighting device;
   controlling, in a first time slot, the lighting device to output a first illumination light source that meets a first predetermined illuminance according to a first illumination requirement and the light sensing value; and
   controlling, in a second time slot, the lighting device to output a second illumination light source that meets a second predetermined illuminance according to a second illumination requirement;
   wherein the first illumination light source and the second illumination light source each have a spectrum that is different from each other in terms of melatonin suppression in humans;
   wherein, according to the first illumination requirement and the second illumination requirement, the lighting device dynamically controls lighting from any one or a combination of a plurality of lighting modules in the lighting device, so as to generate the first illumination light source and the second illumination light source that correspond to the first illumination requirement and the second illumination requirement, respectively;

wherein a product of multiplication of an illuminance and a circadian action factor of the first illumination light source meets the first illumination requirement;

wherein a product of multiplication of an illuminance and a circadian action factor of the second illumination light source meets the second illumination requirement.

18. The dimming method according to claim 17, wherein the lighting device compares the light sensing value with the first predetermined illuminance in the first time slot; and wherein, in order for an illuminance output of the first illumination light source to meet the first predetermined illuminance, the lighting device decreases an illuminance output by the first illumination light source in response to the light sensing value being greater than the first predetermined illuminance, and the lighting device increases the illuminance output by the first illumination light source in response to the light sensing value being less than the first predetermined illuminance.

19. The dimming method according to claim 17, wherein, according to the second illumination requirement and the light sensing value, the lighting device outputs the second illumination light source that meets the second predetermined illuminance in the second time slot; and wherein, in order for an illuminance output of the second illumination light source to meet the second predetermined illuminance, the lighting device decreases an illuminance output by the second illumination light source in response to the light sensing value being greater than the second predetermined illuminance, and the lighting device increases the illuminance output by the second illumination light source in response to the light sensing value being less than the second predetermined illuminance.

20. The dimming method according to claim 17, wherein the first illumination requirement and the second illumination requirement are each an equivalent melanopic lux (EML) value that is different from each other, and any one of the plurality of lighting modules includes at least one light-emitting element.

\* \* \* \* \*